United States Patent [19]

Nardi et al.

[11] Patent Number: 4,482,561

[45] Date of Patent: Nov. 13, 1984

[54] THERAPEUTICALLY EFFECTIVE PIPERIDYL N-(4-QUINOLYL)-ANTHRANILOYLOXYALKANOATES

[75] Inventors: Dante Nardi; Gianni Motta; Rodolfo Testa; Gabriele Graziani, all of Milan, Italy

[73] Assignee: Recordati, S. A., Chemical & Pharmaceutical Co., Chiasso, Switzerland

[21] Appl. No.: 441,093

[22] Filed: Nov. 12, 1982

[30] Foreign Application Priority Data

Nov. 14, 1981 [GB] United Kingdom ............... 8134398

[51] Int. Cl.³ .................. A61K 31/47; C07D 215/44
[52] U.S. Cl. .................. 424/258; 546/161; 546/218; 546/242
[58] Field of Search ............... 424/258; 546/161, 218, 546/242

[56] References Cited

U.S. PATENT DOCUMENTS 3,131,195 4/1964 Rumpf et al. ............... 546/242 X
3,479,360 11/1969 Allais et al. ............... 546/161
4,259,335 3/1981 Beregi et al. ............... 424/258

FOREIGN PATENT DOCUMENTS 2467846 4/1981 France .

Primary Examiner—Donald G. Daus
Assistant Examiner—Diana G. Rivers
Attorney, Agent, or Firm—Burns, Doane, Swecker & Mathis

[57] ABSTRACT

The N-substituted-4-(optionally substituted)-2-, 3- or 4-piperidyl N-(7- or 8-substituted-4-quinolyl)-anthraniloyloxyalkanoates having the structural formula (I):

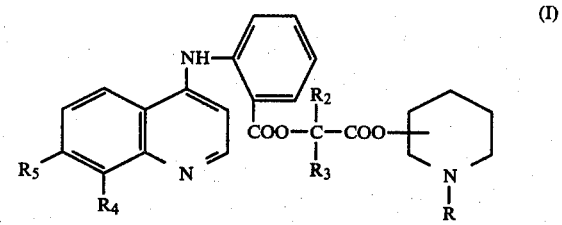

in which R is a straight or branched chain alkyl radical having from 1 to 4 carbon atoms; an alkenyl or alkynyl radical having from 2 to 6 carbon atoms; a benzyl, phenethyl, 4-nitrophenethyl or 4-aminophenethyl radical; or a phenacyl, benzoylethyl, β-hydroxyphenethyl or α-hydroxyphenylpropyl radical, optionally substituted on the phenyl ring by one or more halogen atom, trifluoromethyl, nitro or amino substituents, or an alkyl substituent having from 1 to 4 carbon atoms or an alkoxy substituent having from 1 to 4 carbon atoms; $R_1$ is a hydrogen atom or a phenyl radical; each of $R_2$ and $R_3$ is independently a hydrogen atom or an alkyl radical having from 1 to 4 carbon atoms; one of $R_4$ and $R_5$ is a chlorine atom or a trifluoromethyl radical and the other of $R_4$ and $R_5$ is a hydrogen atom; and the pharmaceutically acceptable salts of such esters; are effective analgesics, anti-inflammatories and antidepressants; are also strong inhibitors of platelet aggregation, and thus too are useful in the treatment of cerebral thrombosis, cerebral and cardiac infarction, and arteriosclerotic disorders.

15 Claims, No Drawings

THERAPEUTICALLY EFFECTIVE PIPERIDYL N-(4-QUINOLYL)-ANTHRANILOYLOXYALKANOATES

FIELD AND SUMMARY OF THE INVENTION

The present invention relates to novel N-substituted-4-(optionally substituted)-2-, 3- or 4-piperidyl N-(7- or 8-substituted-4-quinolyl)-anthraniloyloxyalkanoates, to the pharmaceutically acceptable salts thereof, to processes for the preparation thereof, and to a variety of pharmaceutical compositions comprising same.

The novel N-substituted-4-(optionally substituted)-2-, 3- or 4-piperidyl N-(7- or 8-substituted-4-quinolyl)-anthraniloyloxyalkanoates according to this invention have the structural formula (I):

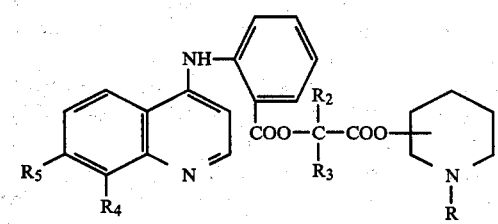

in which R is a straight or branched chain alkyl radical having from 1 to 4 carbon atoms; an alkenyl or alkynyl radical having from 2 to 6 carbon atoms; a benzyl, phenethyl, 4-nitrophenethyl or 4-aminophenethyl radical; or a phenacyl benzoylethyl, β-hydroxyphenethyl or α-hydroxyphenylpropyl radical, optionally substituted on the phenyl ring by one or more halogen atom, trifluoromethyl, nitro or amino substituents, or an alkyl substituent having from 1 to 4 carbon atoms or an alkoxy substituent having from 1 to 4 carbon atoms; $R_1$ is a hydrogen atom or a phenyl radical; each of $R_2$ and $R_3$ is independently a hydrogen atom or an alkyl radical having from 1 to 4 carbon atoms; one of $R_4$ and $R_5$ is a chlorine atom or a trifluoromethyl radical and the other of $R_4$ and $R_5$ is a hydrogen atom; and the pharmaceutically acceptable salts of such esters.

The subject anthraniloyloxyalkanoates according to this invention, and the pharmaceutically acceptable salts thereof, exhibit strong analgesic and anti-inflammatory activity. Same are also strong inhibitors of platelet aggregation and are antidepressants.

DETAILED DESCRIPTION OF THE INVENTION

More particularly according to this invention, the anthraniloyloxyalkanoates having the structural formula (I) are facilely prepared by reacting a substituted piperidine having the structural formula (II):

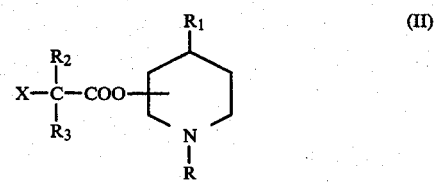

wherein X is a halogen atom and R, $R_1$, $R_2$ and $R_3$ are as hereinbefore defined, with an anthranilic acid derivative having the structural formula (III):

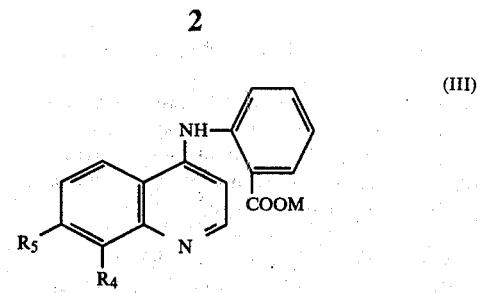

wherein $R_4$ and $R_5$ are also as hereinbefore defined and M is a hydrogen atom or an alkali metal atom.

The intermediates (II), moreover, are themselves novel compounds, and may be prepared by reacting a piperidinol having the structural formula (IV), or hydrochloride thereof:

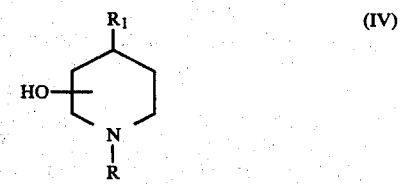

wherein R and $R_1$ are as hereinbefore defined, with a haloalkanoyl chloride having the structural formula (V):

wherein $R_2$, $R_3$ X are also as hereinbefore defined. The condensation is preferably carried out in the presence of an inert organic solvent, such as dimethylformamide. The reactants are typically employed in equimolar proportions, with the reaction temperature ranging from 20° to 50° C. The piperidinols (IV) are readily prepared from piperidinols having the structural formula (VI):

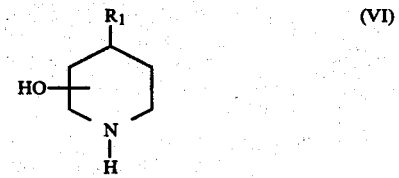

wherein $R_1$ is as hereinbefore defined, by attaching in conventional manner the substituent R to the nitrogen atom.

The anthranilic acid derivatives (III) are per se well known to the art: same can be employed as the free acid or as the alkali metal salts thereof. When the free acid is used, the reaction with the piperidine derivative (II) is carried out in the presence of a solvent, such as dimethylformamide. When an alkali metal salt is employed, the reaction is preferably carried out in dimethylformamide. Whether employing the free acid or the alkali metal salt, an alkali metal carbonate is always added to the reaction medium as an acid binding agent, and the temperature of reaction may range from 20° to 100° C., preferably 50° C. to 100° C. Upon completion of the reaction, the ester thus formed may be purified in conventional manner, for example, by chromatography and crystallization. The compounds of the invention may be employed as such or converted into the pharmaceutically acceptable acid addition salts thereof. These salts according to the invention may easily be prepared from the corresponding free bases utilizing conventional methods, such an addition of an acid to the base dissolved in a suitable solvent.

The present invention additionally features pharmaceutical compositions comprising a pharmaceutically effective amount of a compound having the structural formula (I) as above defined, or a pharmaceutically acceptable salt thereof, in admixture with conventional pharmaceutically acceptable diluent or carrier. Suitable such diluents and carriers, as well as suitable unit dosage amounts, will be apparent to those skilled in this art. Compare, for example, *Remington's Pharmaceutical Sciences*, 4th Edition (1970).

The active compounds/salts according to the invention exhibit good analgesic and anti-inflammatory activity, while displaying but low toxicity. The subject compounds/salts are also strong inhibitors of platelet aggregation and are antidepressants as well. Their $LD_{50}$ values, determined per os in the mouse, are greater than 3000 mg/Kg for a great number of the tested compounds, and the remainder of such values are in excess of 1000 mg/Kg.

The analgesic activity, determined in the mouse utilizing the writhing test [Sigmund et al., *Proc. Soc. Exp. Biol. Med.*, 95, 729 (1957)] and given as $ED_{50}$ mM/Kg ranges from 0.06 to 0.1; the inflammatory activity, determined in the rat utilizing the carragenina test [Winter et al., *Proc. Soc. Exp. Biol. Med.*, 111, 544, (1962)] and given as above, ranges from 0.08 to 0.4.

The compounds/salts of the invention are also highly active as antidepressant agents, and are useful to treat illnesses which entail increased platelet aggregation, e.g., cerebral thrombosis, cerebral infarction, cardiac infarction and arteriosclerotic disorders.

In order to further illustrate the present invention and the advantages thereof, the following specific examples are given, it being understood that same are intended only as illustrative and in nowise limitative.

EXAMPLE 1

Preparation of the Intermediates (II)

11.3 g of Chloroacetylchloride were added to a solution of 11.4 g of N-methyl-3-piperidinol in 20 ml of dimethylformamide, at 20° to 25° C. The reaction product, which formed immediately, was allowed to stand at this temperature for 24 hours. It was then collected by filtration and recrystallized from isopropanol to provide 12.4 g of N-methyl-3-piperidyl chloroacetate hydrochloride. (II, $R=CH_3$, $R_1=R_2=R_3=H$, $X=Cl$), m.p. 168° C.

Repeating the above procedure, but employing N-methyl-4-piperidinol; N-ethyl-4-piperidinol; N-butyl-4-piperidinol; N-benzyl-4-piperidinol; N-methyl-4-phenyl-4-piperidinol; N-phenethyl-4-piperidinol; and N-propargyl-4-piperidinol instead of N-methyl-3-piperidinol, there were respectively obtained N-methyl-4-piperidyl chloroacetate hydrochloride (II, $R=CH_3$, $R_1=R_2=R_3=H$, $X=Cl$), m.p. 177°–179° C.; N-ethyl-4-piperidyl chloroacetate hydrochloride (II, $R=C_2H_5$, $R_1=R_2=R_3=H$, $X=Cl$), m.p. 176°–178° C.; N-butyl-4-piperidyl chloroacetate hydrochloride (II, $R=C_4H_9$, $R_1=R_2=R_3=H$, $X=Cl$), m.p. 205°–206° C.; N-benzyl-4-piperidyl chloroacetate hydrochloride (II, $R=C_6H_5CH_2$, $R_1=R_2=R_3=H$, $X=Cl$), m.p. 214°–215° C.; N-methyl-4-phenyl-4-piperidyl chloroacetate hydrochloride (II, $R=CH_3$, $R_1=C_6H_5$, $R_2=R_3=H$, $X=Cl$), m.p. 181°–183° C.; N-phenethyl-4-piperidyl chloroacetate hydrochloride (II, $R=C_6H_5CH_2CH_2$, $R_1=R_2=R_3=H$, $X=Cl$), m.p. 211°–213° C.; and N-propargyl-4-piperidyl chloroacetate hydrochloride (II, $R=CH_2-C\equiv CH_2$, $R_1=R_2=R_3=H$, $X=Cl$), m.p. 153°–154° C.

EXAMPLE 2

Preparation of N-Methyl-3-piperidyl N-(7-chloro-4-quinolyl)-anthraniloyloxyacetate (I, $R=CH_3$, $R_1=R_2=R_3=R_4=H$, $R_5=Cl$)

4.56 g of N-methyl-3-piperidyl chloroacetate hydrochloride prepared as described in Example 1, 6.4 g of the sodium salt of N-(7-chloro-4-quinolyl)-anthranilic acid and 2.8 g of anhydrous potassium carbonate were heated together under stirring in 40 ml of dimethylformamide at 80° C. for 5 hours. The solution was then cooled and filtered. The solvent was evaporated off in vacuo at 50°–70° C. The oily residue thus obtained was treated with water and sodium carbonate, and then extracted with ethyl acetate. The organic phase was washed with water and dried on anhydrous sodium sulfate. The ethyl acetate was evaporated off, and the reaction product was purified by chromatography on an alumina column using chloroform as eluant. The fractions were combined and concentrated to provide 2.5 g of the title product, m.p. 135°–137° C.

EXAMPLE 3

Preparation of N-Methyl-4-piperidyl N-(7-chloro-4-quinolyl)-anthraniloyloxyacetate (I, $R=CH_3$, $R_1=R_2=R_3=R_4=H$, $R_5=Cl$)

Repeating the procedure of Example 2, but employing N-methyl-4-piperidyl chloroacetate hydrochloride, prepared as described in Example 1, instead of N-methyl-3-piperidyl chloroacetate hydrochloride, there was obtained the title compound, m.p. 150°–151° C.

EXAMPLE 4

Preparation of N-Methyl-4-phenyl-4-piperidyl N-(7-chloro-4-quinolyl)-anthraniloyloxyacetate (I, $R=CH_3$, $R_1=C_6H_5$, $R_2=R_3=R_4=H$, $R_5=Cl$)

15.2 g of N-methyl-4-phenyl-4-piperidyl chloroacetate hydrochloride, prepared as described in Example 1, 16 g of the sodium salt of N-(7-chloro-4-quinolyl)-anthranilic acid and 7 g of anhydrous potassium carbonate were heated together in 100 ml of dimethylformamide, following the procedure described in Example 2. 10.5 g of the title compound were obtained and were recrystallized from methanol, m.p. 148°–149° C.

EXAMPLE 5

Preparation of N-Ethyl-4-piperidyl N-(7-chloro-4-quinolyl)-anthraniloyloxyacetate (I, $R=C_2H_5$, $R_1=R_2=R_3=R_4=H$, $R_5=Cl$)

Repeating the procedure of Example 2, but using N-ethyl-4-piperidyl chloroacetate hydrochloride, prepared as described in Example 1, instead of N-methyl-3-piperidyl chloroacetate hydrochloride, there was obtained the title compound, m.p. 132°–134° C.

EXAMPLE 6

Preparation of N-Butyl-4-piperidyl N-(7-chloro-4-quinolyl)-anthraniloyloxyacetate (I, R=C$_4$H$_9$, R$_1$=R$_2$=R$_3$=R$_4$=H, R$_5$=Cl)

Repeating the procedure of Example 2, but using N-butyl-4-piperidyl chloroacetate hydrochloride, prepared as described in Example 1, instead of N-methyl-3-piperidyl chloroacetate hydrochloride, there was obtained the title compound, m.p. 111°–112° C.

EXAMPLE 7

Preparation of N-Methyl-4-piperidyl N-(7-trifluoromethyl-4-quinolyl)-anthraniloyloxyacetate (I, R=CH$_3$, R$_1$=R$_2$=R$_3$=R$_4$=H, R$_5$=CF$_3$)

A mixture of 9.12 g of N-methyl-4-piperidyl chloroacetate hydrochloride, prepared as described in Example 1, 14.5 g of the sodium salt of N-(7-trifluoromethyl-4-quinolyl)-anthranilic acid and 5.6 g of anhydrous potassium carbonate was heated at 80° C. for 5 hours in 80 ml of dimethylformamide. The mixture was cooled, filtered, and evaporated to dryness in vacuo. Water was added to the oily residue obtained, and the mixture was extracted with ethyl acetate. The extract was dried on anhydrous sodium sulfate, and the solvent was evaporated off. The residue was washed with diethyl ether. The etheric phase was purified chromatographically on an alumina column using chloroform as eluant. The title compound, m.p. 101°–102° C., was recrystallized from hexane.

EXAMPLE 8

Preparation of N-Benzyl-4-piperidyl N-(7-chloro-4-quinolyl)-anthraniloyloxyacetate (I, R=C$_6$H$_5$CH$_2$, R$_1$=R$_2$=R$_3$=R$_4$=H, R$_5$=Cl)

By repeating the procedure of Example 7, but commencing by heating 12.16 g of N-benzyl-4-piperidyl chloroacetate hydrochloride, prepared as described in Example 1, 12.8 g of the sodium salt of N-(7-chloro-4-quinolyl)-anthranilic acid and 5.6 g of anhydrous potassium carbonate in 80 ml of dimethylformamide, there were obtained 9.8 g of the title compound, m.p. 125°–126° C.

EXAMPLE 9

Preparation of N-Phenethyl-4-piperidyl-(7-chloro-4-quinolyl)-anthraniloyloxyacetate (I, R=C$_6$H$_5$CH$_2$CH$_2$, R$_1$=R$_2$=R$_3$=R$_4$=H, R$_5$=Cl)

The title compound, m.p. 118°–120° C., was prepared (yield 6 g) from 15.9 g of N-phenethyl-4-piperidyl chloroacetate hydrochloride, prepared as described in Example 1, and 16 g of the sodium salt of N-(7-chloro-4-quinolyl)-anthranilic acid, following the procedure described in Example 7.

EXAMPLE 10

Preparation of N-Phenacyl-4-piperidyl N-(7-chloro-4-quinolyl)-anthraniloyloxyacetate (I, R=C$_6$H$_5$COOCH$_2$, R$_1$=R$_2$=R$_3$=R$_4$=H, R$_5$=Cl)

A mixture of 20 g of N-phenacyl-4-piperidyl chloroacetate hydrochloride, 19.2 g of the sodium salt of N-(7-chloro-4-quinoyl)-anthranilic acid, 8.4 g of potassium carbonate and 120 ml of dimethylformamide, was heated at 80° C. for 6 hours. When the heating was completed, the inorganic salts were filtered off and the solution evaporated to dryness in vacuo. The residue thus obtained was treated with water and the solid collected by filtration was purified on a silica gel column using ethyl acetate as eluant. Intermediate fractions containing the title compound were evaporated to dryness and the solid thus obtained was crystallized from acetone. M.p. 154°–155° C., yield 9 g (27%).

EXAMPLE 11

Preparation of N-(p-nitro-phenethyl)-4-piperidyl N-(7-chloro-4-quinolyl)-anthraniloyloxyacetate (I, R=4 nitro-phenethyl, R$_5$=Cl, R$_1$=R$_2$=R$_3$=R$_4$=H)

A mixture of 18.1 g of N-(p-nitro-phenethyl)-4-piperidyl chloroacetate hydrochloride, 16 g of the sodium salt of N-(7-chloro-4-quinolyl)-anthranilic acid and 7 g of potassium carbonate in 100 ml of dimethylformamide was refluxed for 5 hours at 80° C. Upon completion of the reaction, the insoluble inorganic salts were filtered off and the mixture was evaporated to dryness at 50°–70° C. The oily residue was treated with water and the solid, collected by filtration, was purified on a silica gel column using ethyl acetate as eluant. The fractions containing the pure title compound were combined, the solvent was evaporated off in vacuo and the residue crystallized from ethyl acetate. M.p. 135°–136° C., yield 19.5 g (66%).

0.2 g of 5% palladium-on-carbon was added to 5.9 g of the aforesaid product in 100 ml of acetic acid, and the entire mass was hydrogenated. When the absorption of hydrogen was complete the catalyst was filtered off, the solution was diluted with 150 ml of water, a 20% solution of sodium carbonate was added until a pH of 8 was attained and the solution was extracted with ethyl acetate. The solvent was then evaporated off and the residue chromatographed on a silica gel column using acetone as eluant. The first fractions were collected, the solvent was evaporated off and the residue purified by conversion into its hydrochloride.

| NMR (CDCl$_3$) | | | | |
|---|---|---|---|---|
| δ | 8.6 | 1H | (d) | quinoline; |
| | 4.9 | 1H | (m) | piperidine; |
| | 4.85 | 2H | (s) | —O—CH$_2$—COO; |
| | 3.35 | 2H | (bs) | —NH$_2$. |

M.p. 214°–216° C. (with decomposition). In formula (I), R=4-amino-phenethyl.

EXAMPLE 12

Preparation of N-Allyl-4-piperidyl N-(7-chloro-4-quinolyl)-anthraniloyloxyacetate (I, R=CH$_2$—CH=CH$_2$, R$_5$=Cl, R$_1$=R$_2$=R$_3$=R$_4$=H)

A mixture of 12.7 g of N-allyl-4-piperidyl chloroacetate hydrochloride, 16 g of the sodium salt of N-(7-chloro-4-quinolyl)-anthranilic acid and 7 g of anhydrous potassium carbonate in 100 ml of dimethylformamide was stirred and heated at 80° C. for 5 hours. Upon completion of the reaction, the insoluble inorganic salts were filtered off and the mixture was evaporated to dryness in vacuo at 50°–70° C. The oily residue was treated with water and the solid, collected by filtration, was purified on a silica gel column using ethyl acetate as eluant. The fractions containing the title compound were combined, the solvent evaporated off in vacuo and the residue crystallized from ethanol. M.p. 115°–117° C., yield 7.4 g (31%).

Employing N-propargyl-4-piperidyl chloroacetate instead of N-allyl-4-piperidyl chloroacetate, the corresponding ester was obtained. Crystallization from ethyl acetate, m.p. 111°–113° C., yield 10.5 g (44%), employing same amounts of starting materials (I, R=CH$_2$—C≡CH).

EXAMPLE 13

Preparation of N-benzyl-4-piperidyl N-(8-trifluoromethyl-4-quinolyl)-anthraniloyloxyacetate (I, R=benzyl, R$_1$=R$_2$=R$_3$=R$_4$=H, R$_4$=CF$_3$)

Repeating the procedure of Example 12, but utilizing 17.7 g of N-benzyl-4-piperidyl chloroacetate hydrochloride, 15.2 g of the sodium salt of the corresponding anthranilic acid and 7 g of potassium carbonate, 17 g of the title compound were obtained. M.p. 99°–100° C., yield 60%.

EXAMPLE 14

Preparation of N-Methyl-4-phenyl-4-piperidyl N-(8-trifluoromethyl-4-quinolyl)-anthraniloyloxyacetate (I, R=CH$_3$, R$_1$=Ph, R$_2$=R$_3$=R$_5$=H, R$_4$=CF$_3$)

A mixture of 1.52 g of N-methyl-4-phenyl-4-piperidyl chloroacetate hydrochloride, 1.77 g of the sodium salt of N-(8-trifluoromethyl-4-quinolyl)-anthranilic acid and 0.7 g of potassium carbonate in 10 ml of dimethylformamide was stirred for 48 hours at 20°–25° C. Upon completion of the reaction, the inorganic salts were filtered off. The solution was evaporated to dryness and treated with water, and the solid collected by filtration. This solid was then refluxed with hexane, filtered and recrystallized from hexane to provide the title compound. M.p. 144°–145° C., yield 1 g (35%).

EXAMPLE 15

Preparation of N-Methyl-4-piperidyl α-[N-(7-chloro-4-quinolyl)-anthraniloyloxy]-propionate (I, R=CH$_3$, R$_1$=R$_2$=R$_4$=H, R$_3$=CH$_3$, R$_5$=Cl)

A mixture of the sodium salt of N-(7-chloro-4-quinolyl)-anthranilic acid, 2.5 g of N-methyl-4-piperidyl α-bromopropionate and 20 ml of dimethylformamide was stirred and heated at 80° C. for 5 hours. Upon completion of the reaction, after cooling, the inorganic salts were filtered off and the solvent evaporated off in vacuo. The oily residue was purified on alumina column using chloroform as eluant. The fractions containing the desired product were combined and the solvent evaporated off. Yield 4 g (85%).

The structure of the oily product was determined by

| NMR (CDCl$_3$) | | | | |
|---|---|---|---|---|
| δ | 10.4 | 1H | (s) | —NH; |
|   | 8.6  | 1H | (d) | quinoline; |
|   | 5.3  | 1H | (q) | O—CH—COO; |
|   | 4.85 | 1H | (m) | piperidine; |
|   | 2.15 | 3H | (s) | N—CH$_3$; |
|   | 1.62 | 3H | (d) | —O—CH(CH$_3$)—COO. |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A compound having the structural formula (I):

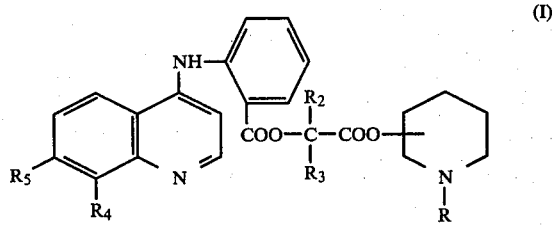

in which R is a straight or branched chain alkyl radical having form 1 to 4 carbon atoms; an alkenyl or alkynyl radical having from 2 to 6 carbon atoms; a benzyl, phenethyl, 4-nitrophenethyl or 4-aminophenethyl radical; or a phenacyl, benzoylethyl, β-hydroxyphenethyl or α-hydroxyphenylpropyl radical, optionally substituted on the phenyl ring by one or more halogen atom, trifluoromethyl, nitro or amino substituents, or an alkyl or alkoxy substituent having from 1 to 4 carbon atoms; R$_1$ is a hydrogen atom or a phenyl radical; each of R$_2$ and R$_3$ is independently a hydrogen atom or an alkyl radical having from 1 to 4 carbon atoms; one of R$_4$ and R$_5$ is a chlorine atom or a trifluoromethyl radical and the other of R$_4$ and R$_5$ is a hydrogen atom; and the pharmaceutically acceptable salts thereof.

2. The compound as defined by claim 1, wherein R is alkyl.

3. The compound as defined by claim 1, wherein R is alkenyl.

4. The compound as defined by claim 1, wherein R is alkynyl.

5. The compound as defined by claim 1, wherein R is benzyl.

6. The compound as defined by claim 1, wherein R is phenethyl.

7. The compound as defined by claim 1, wherein R is 4-nitrophenethyl.

8. The compound as defined by claim 1, wherein R is 4-aminophenethyl.

9. The compound as defined by claim 1, wherein R is phenacyl, benzoylethyl, β-hydroxyphenethyl or α-hydroxyphenylpropyl.

10. The compound as defined by claim 9, wherein the phenyl moiety comprising the R substituent is substituted.

11. The compound as defined by claim 1, wherein R$_1$ is phenyl.

12. The compound as defined by claim 1, selected from the group consisting of N-methyl-3-piperidyl N-(7-chloro-4-quinolyl)-anthraniloyloxyacetate; N-methyl-4-piperidyl N-(7-chloro-4-quinolyl)-anthraniloyloxyacetate; N-methyl-4-phenyl-4-piperidyl N-(7-chloro-4-quinolyl)-anthraniloyloxyacetate; N-ethyl-4-piperidyl N-(7-chloro-4-quinolyl)-anthraniloyloxyacetate; N-butyl-4-piperidyl N-(7-chloro-4-quinolyl)-anthraniloyloxyacetate; N-methyl-4-piperidyl N-(7-trifluoromethyl-4-quinolyl)-anthraniloyloxyacetate; N-benzyl-4-piperidyl N-(7-chloro-4-quinolyl)-anthraniloyloxyacetate; N-phenethyl-4-piperidyl N-(7-chloro-4-quinolyl)-anthraniloyloxyacetate; N-phenacyl-4-piperidyl N-(7-chloro-4-quinolyl)-anthraniloyloxyacetate; N-(p-nitro-phenethyl)-4-piperidyl N-(7- chloro-4-quinolyl)-anthraniloyloxyacetate; N-(p-aminophenethyl)-4-piperidyl N-(7-chloro-4-quinolyl)-anthraniloyloxyacetate; N-allyl-4-piperidyl N-(7-chloro-4-quinolyl)-anthraniloyloxyacetate; N-propargyl-4-piperidyl N-(7-chloro-4-quinolyl)-anthraniloyloxyacetate; N-benzyl-4-piperidyl N-(8-trifluoromethyl-4-quinolyl)-anthraniloyloxyacetate; N-methyl-4-phenyl-4-piperidyl N-(8-trifluoromethyl-4-quinolyl)-anthraniloyloxyacetate; and N-methyl-4-piperidyl α-[N-(7-chloro-4-quinolyl)-anthraniloyloxy]-propionate.

13. A pharmaceutical composition of matter comprising an analgesic, anti-inflammatory, antidepressant or platelet aggregation inhibiting amount of the compound as defined by claim 1, or pharmaceutically acceptable salt thereof, and a pharmaceutically acceptable diluent or carrier therefor.

14. The method for eliciting an analgesic, anti-inflammatory, antidepressant or platelet aggregation inhibiting response in a warm-blooded animal, comprising administering to a warm-blooded animal in need of such treatment, a therapeutically effective amount of the compound as defined by claim 1, or pharmaceutically effective salt thereof.

15. The method for eliciting an analgesic, anti-inflammatory, antidepressant or platelet aggregation inhibiting response in a warm-blooded animal, comprising administering to a warm-blooded animal in need of such treatment, a therapeutically effective amount of the pharmaceutical composition of matter as defined by claim 13.

* * * * *

UNITED STATES PATENT AND TRADEMARK OFFICE
CERTIFICATE OF CORRECTION

PATENT NO. : 4,482,561

DATED : November 13, 1984

INVENTOR(S) : DANTE NARDI et al

It is certified that error appears in the above-identified patent and that said Letters Patent is hereby corrected as shown below:

Title page:

IN THE ABSTRACT:

Kindly change the formula to read:

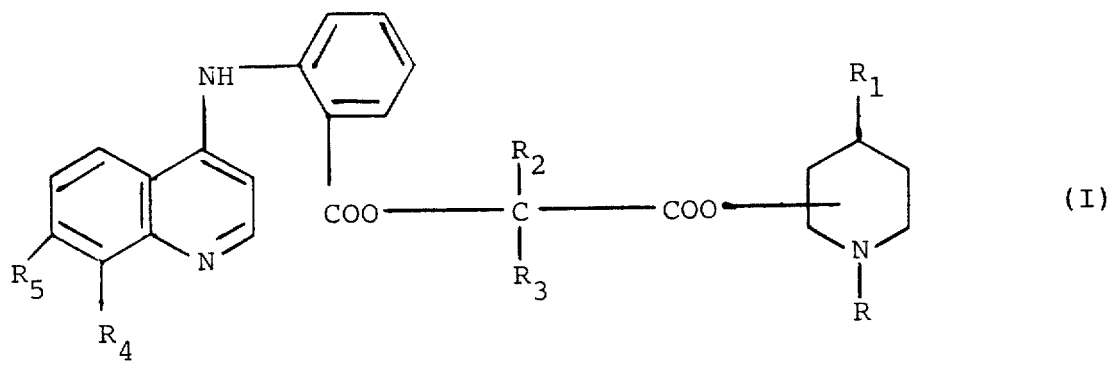

Column 1, lines 18-27, kindly change the formula to read:

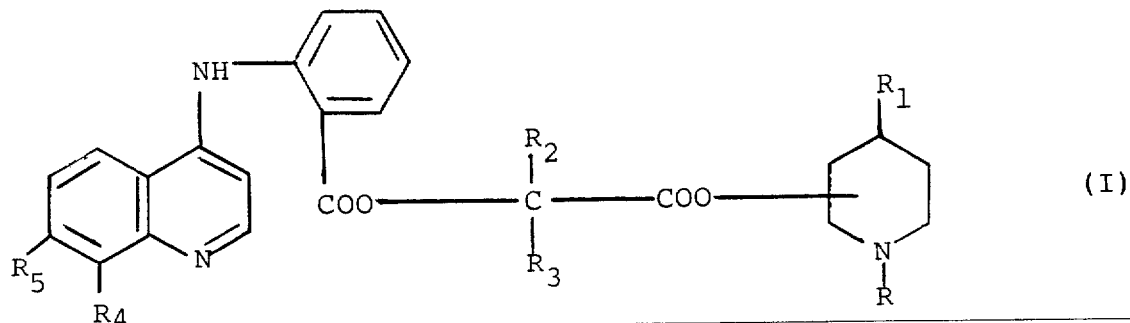

UNITED STATES PATENT AND TRADEMARK OFFICE
CERTIFICATE OF CORRECTION

PATENT NO. : 4,482,561
DATED : November 13, 1984
INVENTOR(S) : DANTE NARDI et al It is certified that error appears in the above-identified patent and that said Letters Patent is hereby corrected as shown below:

Claim 1, lines 6-15, kindly change the formula to read:

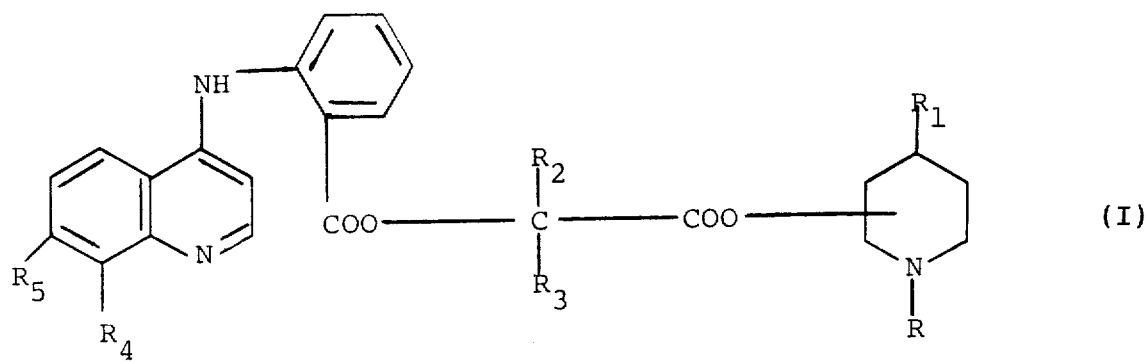

Signed and Sealed this

Sixteenth Day of April 1985

[SEAL]

Attest:

DONALD J. QUIGG

Attesting Officer   Acting Commissioner of Patents and Trademarks